United States Patent [19]

Shaw et al.

[11] 4,378,309

[45] Mar. 29, 1983

[54] CATALYST COMPOSITIONS FOR THE PREPARATION OF UNSATURATED ACIDS

[75] Inventors: Wilfrid G. Shaw, Lyndhurst; David B. Terrill, Bedford Heights, both of Ohio

[73] Assignee: Standard Oil Company (SOHIO), Cleveland, Ohio

[21] Appl. No.: 315,804

[22] Filed: Oct. 28, 1981

Related U.S. Application Data

[63] Continuation of Ser. No. 213,426, Dec. 5, 1980, abandoned, which is a continuation of Ser. No. 839,681, Oct. 5, 1977, abandoned, which is a continuation of Ser. No. 708,812, Jul. 26, 1976, Pat. No. 4,082,698.

[51] Int. Cl.³ .................. B01J 23/14; B01J 23/22; B01J 23/28; B01J 23/72
[52] U.S. Cl. ................................................ 252/469

[58] Field of Search ................ 252/469; 562/535

[56] References Cited

U.S. PATENT DOCUMENTS 3,736,354  5/1973  Yanagita et al. .............. 252/469 X
4,014,927  3/1977  Kadowaki ..................... 252/469 X

*Primary Examiner*—W. J. Shine
*Attorney, Agent, or Firm*—Larry W. Evans; Herbert D. Knudsen; David J. Untener

[57] ABSTRACT

The present invention relates to a catalyst composition consisting of oxide complexes of vanadium, molybdenum and copper plus an additional metal oxide selected from the group consisting of antimony and germanium or mixtures thereof. These catalysts are especially useful for producing acrylic acid from acrolein and for producing methacrylic acid from methacrolein.

1 Claim, No Drawings

CATALYST COMPOSITIONS FOR THE PREPARATION OF UNSATURATED ACIDS

CROSS REFERENCE TO RELATED APPLICATION

This application is a continuation of Ser. No. 213,426 filed Dec. 5, 1980, now abandoned, which is a continuation of Ser. No. 839,681, filed Oct. 5, 1977, now abandoned, which is a continuation of Ser. No. 708,812, filed July 26, 1976, now U.S. Pat. No. 4,082,698.

BACKGROUND OF THE INVENTION

Catalyst compositions similar to those of the invention are disclosed in Belgian Pat. No. 773,851 which discloses catalysts of the composition molybdenum, vanadium, tungsten and antimony and one or more of the oxides of lead, silver, tin, titanium, copper and bismuth. U.S. Pat. No. 3,736,354 discloses the catalyst compositions containing the oxides of vanadium, molybdenum and germanium and the oxides of vanadium, molybdenum and copper. German Pat. No. 2,414,797 discloses a catalyst for the production of acrylic and methacrylic acids from acrolein or methacrolein which contains the metal oxides of molybdenum, vanadium, copper and at least one element of the group of iron, cobalt, nickel and magnesium. U.S. Pat. No. 3,725,472 discloses a catalyst for the oxidation $\alpha\beta$-unsaturated carbonylic compounds to the corresponding unsaturated acids employing a catalyst containing the oxides of molybdenum, vanadium and antimony.

None of the foregoing patents, however, disclose the catalyst compositions of the present invention wherein unexpectedly high yields of unsaturated carboxylic acids are obtained from the corresponding unsaturated aldehydes in the presence of these catalysts.

SUMMARY OF THE INVENTION

The present invention is a catalyst composition consisting of oxides or oxide complexes that contain catalytically significant amounts of vanadium, molybdenum and copper, plus an additional metal oxide wherein the additional metal may be antimony or germanium or both. These catalysts are especially effective for preparing acrylic acid from acrolein and the preparation of methacrylic acid from methacrolein. The catalysts are also highly effective for oxidation reactions such as the oxidation of butadiene to maleic anhydride and the oxidation of the butenes and the aromatics to various oxygenated compounds. The catalysts of the present invention are highly reactive and are capable of very selectively oxidizing acrolein to acrylic acid with little acetic acid being formed.

The method of preparation of these catalysts is not deemed critical. Normally, the catalysts of the invention are prepared by mixing the catalyst ingredients in the proper proportions in an aqueous mixture, drying the resulting aqueous slurry with or without a reducing agent and calcining the product. The ingredients employed in the preparation of the catalysts can be the oxides, halides, nitrates, acetates or other salts of the particular compound added, and particularly preferred is the use of water soluble salts of the metal components. If a support is used, the material comprising the support may be incorporated into the catalyst along with the other ingredients or the catalytic ingredient may be coated on an inert core. After the catalyst ingredients have been combined to form an aqueous slurrly, the slurry is evaporated to dryness, and the dried solid obtained is heated in the presence of air at temperatures between about 200° and 600° C. This calcination can take place outside of the catalytic reactor or an in situ activation could be utilized.

More specifically, the catalysts of the invention are described by the following empirical formula:

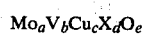

$$Mo_aV_bCu_cX_dO_e$$

wherein X is a member selected from the group consisting of antimony and germanium or both,
and wherein
 a is 6 to about 18
 b, c and d each are about 0.1 to about 6; and
 e is the number of oxygens required to satisfy the valance requirements of the other elements present.

In addition to the active catalytic ingredients the catalysts of the invention may contain a support material, Suitable support materials include silica, alumina, zirconia, titania, silicon carbide, boron phosphate and the like. A preferred support material is Alundum. Also contemplated in this invention is the incorporation of metal oxide promoters in the catalyst compositions to further enhance their activity.

As noted above, the catalysts of the invention are useful in a number of different oxidation reactions. Preferred among these reactions is the production of unsaturated acids from the corresponding unsaturated aldehydes. In such a process, acrylic acid or methacrylic acid is produced by reacting acrolein or methacrolein with molecular oxygen in the presence of steam at a temperature of about 200° to about 500° C. Of special interest is the preparation of acrylic acid from acrolein because of the extremely desirable results obtained.

The oxidation of unsaturated aldehydes to obtain the corresponding acid is well known in the art. Basically, the invention, with respect to the process, is the use of the new catalyst within the parameters of the known art process.

The known process involves the contacting of the unsaturated aldehyde with molecular oxygen in the presence of steam at a temperature of about 200° to about 500° C. The ratio of the reactants may vary widely with molar ratios of molecular oxygen to aldehyde of about 0.5 to about 5 moles normally being employed. Molecular oxygen is most conveniently added as air. The amount of steam may vary widely from the small amount generated in the reaction to 20 or more moles of steam per mole of aldehyde. In the preferred practice of the invention, about 1 to about 10 moles of steam are added to the reactant feed.

The reaction may be conducted in a fixed- or fluid-bed reactor using atmospheric, superatmospheric or subatmospheric pressure. The apparent contact time may vary considerably with contact times of a fraction of a second to 20 seconds or more normally being employed.

SPECIFIC EMBODIMENTS

Comparative Examples A–C and Examples 1 and 2

The catalysts of the invention were prepared and compared to the known catalyst compositions of U.S. Pat. No. 3,736,354, (Examples A and B), U.S. Pat. No. 3,725,472 (Example C) and German Pat. No. 2,414,797 (Example D) for the reaction of the oxidation of acrolein to acrylic acid.

The catalysts of the comparative examples were prepared as follows.

COMPARATIVE EXAMPLE A $Mo_{12}V_3Cu_{0.5}O_{44.0}$

To 250 cc of hot distilled water was added 6.88 g of ammonium metavanadate. After approximately 15 minutes of heating and stirring, the reagent was dissolved and 41.54 g of ammonium heptamolybdate was added to the solution. The ammonium heptamolybdate and 1.96 g of cupric acetate which was added subsequently, dissolved almost immediately. The solution was evaporated to near dryness with continual stirring and the catalyst was then placed in a drying over at 110°–120° C. for 16 hours. The dried material was crushed and ground through a 50 mesh screen. A sufficient amount of catalyst was employed to coat 3/16' spheres to achieve a twenty weight percent coating on the spheres. The coated spheres were then dried at 110°–120° C. for three hours and then activated by heat treating at 370° C. for two hours.

COMPARATIVE EXAMPLE B $Mo_{12}V_3GeO_{45.4}$

The procedure of comparative Example A was repeated with the exception that 6.67 g of ammonium metavanadate and 40.27 g of ammonium heptamolybdate were used, and 1.99 g of germanium dioxide was employed in place of the copper acetate.

COMPARATIVE EXAMPLE C $Mo_{12}V_3Sb\ O_{45.0}$

The procedure of Comparative Example A was repeated using 6.54 g of ammonium metavanadate and 39.50 g of ammonium heptamolybdate, and 2.71 g antimony oxide ($Sb_2O_3$) was employed in place of the copper acetate.

COMPARATIVE EXAMPLE D $Mo_{12}V_3Cu_{0.5}Ni\ O_{45.5}$

The procedure of Comparative Example A was repeated using 6.61 g of ammonium metavanadate, 39.93 g of ammonium heptamolybdate, 1.88 g of cupric acetate and 5.47 g of nickel nitrate hexahydrate, these ingredients being added to the aqueous solution in that order.

The preparation of the catalysts in the Examples representative of the invention are given below.

EXAMPLE 1

$Mo_{12}V_3Cu_{0.5}GeO_{46.0}$

To 250 cc of hot distilled water was added 6.55 g of ammonium metavanadate. After approximately 15 min. of heating and stirring, the reagent was dissolved and 39.52 g of ammonium heptamolybdate was added to the solution. The ammonium heptamolybdate and 1.86 g of cupric acetate which was added subsequently dissolved almost immediately. 1.95 g of germanium dioxide ($GeO_2$) was added and the solution was evaporated to near dryness with continual stirring. The catalyst was then placed in a drying oven for 16 hours at 110°–120° C. and the dried material was crushed and ground to pass through a 50 mesh screen. A sufficient amount of catalyst was employed to coat 3/16" spheres of Alundum to achieve a twenty weight percent coating on the spheres. The coated spheres were then dried at 110°–120° C. for three hours and then activated by heat treating at 370° C. for two hours.

EXAMPLE 2

$Mo_{12}V_3Cu_{0.5}SbO_{46.5}$

The procedure of Example 1 was repeated using 6.38 g of ammonium metavanadate, 38.49 g of ammonium heptamolybdate and 1.81 g of cupric acetate, followed by the addition of 2.64 g of antimony oxide ($Sb_2O_3$) in place of germanium dioxide.

The catalysts prepared above were placed in a fixed bed reactor constructed of a 1.0 cm. inside diameter stainless steel tube having a reaction zone of 20 cc. capacity. The reactor was heated in a split block furnace. The reactor was fed with a mixture of acrolein/air/$N_2$/steam in the molar ratio of 1/8.5/2.5/6. The apparent contact time was 2 seconds. The temperature of the surrounding block is given in Table 1. The results are also given in Table 1 using the following definitions:

$$\text{Single Pass Yield, \%} = \frac{\text{Moles of product recovered} \times 100}{\text{Moles of acrolein fed}}$$

$$\text{Conversion, \%} = \frac{\text{Moles of acrolein reacted} \times 100}{\text{Moles of acrolein fed}}$$

$$\text{Selectivity, \%} = \frac{\text{Moles of acrylic acid recovered} \times 100}{\text{Moles of acrolein reacted}}$$

TABLE I

OXIDATION OF ACROLEIN TO ACRYLIC ACID

| EXAMPLE | CATALYST (1) | TEMP., °C. | % SINGLE PASS YIELD ACRYLIC ACID | % SINGLE PASS YIELD ACETIC ACID | % CONVERSION | % SELECTIVITY |
|---|---|---|---|---|---|---|
| Comp. A | $Mo_{12}V_3Cu_{0.5}O_{44.0}$ | 342 | 52.6 | 1.9 | 73.5 | 71.6 |
| Comp. B | $Mo_{12}V_3GeO_{45.5}$ | 321 | 91.2 | 1.4 | 97.5 | 93.5 |
| Comp. C | $Mo_{12}V_3SbO_{45.0}$ | 356 | 49.2 | 1.4 | 66.1 | 74.4 |
| Comp. D | $Mo_{12}V_3Cu_{0.5}NiO_{45.5}$ | 341 | 48.2 | 1.5 | 63.6 | 75.8 |
| 1 | $Mo_{12}V_3Cu_{0.5}GeO_{46.0}$ | 299 | 95.7 | 1.0 | 99.6 | 96.1 |
| 2 | $Mo_{12}V_3Cu_{0.5}SbO_{46.5}$ | 330 | 90.9 | 2.0 | 99.4 | 91.4 |

(1) 20% active component on 3/16" Alundum spheres.

What is claimed is:

1. A catalyst composition having the empirical formula:

$$Mo_aV_bCu_cGe_dO_e$$

wherein a is a number from about 6 to about 18;

b, c and d each are about 0.1 to about 6;

and e is the number of oxygens required to satisfy the valence requirements of the other elements present.

* * * * *